United States Patent [19]

Amino et al.

[11] Patent Number: 5,362,311
[45] Date of Patent: Nov. 8, 1994

[54] ARTIFICIAL HIP JOINT

[75] Inventors: Hirokazu Amino; Yoshinori Shiraiwa, both of Kyoto, Japan; Ian C. Clarke, Santa Monica, Calif.

[73] Assignee: Kyocera Corporation, Kyoto, Japan

[21] Appl. No.: 461,385

[22] Filed: Jan. 5, 1990

[51] Int. Cl.⁵ ................................................. A61F 2/30
[52] U.S. Cl. ........................................................ 623/22
[58] Field of Search .................................... 623/18, 22

[56] References Cited

U.S. PATENT DOCUMENTS

| | | |
|---|---|---|
| 4,012,795 | 3/1977 | Doore et al. |
| 4,032,994 | 7/1977 | Frey ........................... 623/22 |
| 4,058,856 | 11/1977 | Doerre et al. ............... 623/22 |
| 4,268,919 | 5/1981 | Zeibig . |
| 4,318,190 | 3/1982 | Cortesi . |
| 4,687,488 | 8/1987 | Frey ........................... 623/22 |
| 4,842,605 | 6/1989 | Sonnerat et al. ............ 623/22 |
| 4,921,500 | 5/1990 | Averill et al. . |
| 4,964,869 | 10/1990 | Auclair et al. . |

FOREIGN PATENT DOCUMENTS

| | | | |
|---|---|---|---|
| 0193681 | 9/1986 | European Pat. Off. ............ 623/18 |
| 2618763 | 11/1976 | Germany ........................... 623/18 |
| 0011665 | 11/1978 | Germany ........................... 623/22 |
| 3023354 | 4/1981 | Germany . |
| 3802213 | 7/1989 | Germany ........................... 623/18 |

OTHER PUBLICATIONS

Co-pending application Ser. No. 370,450, filed Jun. 23, 1989.

*Primary Examiner*—David Isabella
*Attorney, Agent, or Firm*—Spensley Horn Jubas & Lubitz

[57] ABSTRACT

In an artificial hip joint, in which a tapered cone of a metallic stem is inserted into a tapered hole of a ceramic stem head to be fixed, a truncated conical sleeve having a thickness of 50 μm to 5.0 mm is compressedly held between a wall surface of the tapered hole and an outer circumferential surface of the tapered cone such that they are taperedly engaged with each other. With this artificial hip joint, an increased strength of the stem head, easy production, miniaturization, increased useful life time, safety in use, and the protection of the tapered cone are achieved.

6 Claims, 3 Drawing Sheets

ARTIFICIAL HIP JOINT

BACKGROUND OF THE INVENTION

1. Field of the Invention

The present invention relates to an artificial hip joint adapted to replace and restore the hip joint of a human being.

2. Prior Art

Typically, an artificial joint, and more particularly an artificial hip joint, comprises a stem head ball (hereinafter referred to as a "stem head") integrally fixed to a stem or attached by tapered engagement of the stem with the stem head by the use of metal, such as stainless steel, cobalt chromium based alloy or titanium alloy, in such a manner that the stem is fixedly inserted into a femur by the use of cement in the gap between them. On the other hand, a socket for receiving the stem head therein is made of polyethylene and fixedly mounted on the pelvis with cement.

In recent years, it has become general practice to fixedly mount the stem head on the pointed end of a metal stem by tapered cone engagement, and the kind of the material used in the construction is mostly stainless steel, cobalt chromium based alloy and the like.

The artificial joint constructed of the material described is adapted to vary the height (neck-length) of the joint when the stem is fixedly mounted on the stem head by changing the depth and the diameter of the tapered hole in the head. This joint system is becoming the common practice for the artificial hip joint.

On the other hand, alumina ceramics, low in friction and abrasion by a combination of the material with polyethylene, is recognized as a material for the stem head because of its excellence in clinical performance and has come to be used in many cases. However, a major concern in the past has been the possibility of damage to the stem head due to unfitness in engagement of the pointed end portion of the metallic stem with the tapered hole formed in a ceramic stem head when the ceramic stem head is used. It has been said that a load of up to 5 times the body weight of a human being acts upon the condyle of the human being, and accordingly, a load of up to about 400 kg repeatedly acts upon a person having a body weight of 80 kg. That is to say, the head is always subjected to large cyclic forces for a long time, so that an exceedingly high strength is required. Also from a view point of durability over a long period of time, a high margin of safety is demanded of the hip joint. However, the reality is that, when the proximal end of the stem is fitted into the tapered hole of the ceramic stem head, problems can occur in that, for example, even the misfit caused by fine foreign debris, such an fine bone pieces, straying into the gap between the hole and the end of the stem would lead to an uneven distribution of stress within the tapered hole of the stem head and induce fracture of the stem head due to the local concentration of stress.

A means to solve the problems above described makes it necessary to bring the tapered hole formed in the stem head into complete tapered engagement with the tapered cone formed in the pointed end portion of the stem.

It is, however, impossible to bring both into highly precise agreement with each other by conventional machining.

And, there have been made various proposals such as a proposal for circumferentially forming regularly-arranged concavities and convexities on the surface of the tapered cone of the metal stem (for example, U.S. Pat. No. 4,012,795), or a proposal for making the tapered cone of the stem hollow or forming slits in the cone and deforming the tapered cone of the stem so as to bring the tapered cone of the stem into agreement with the wall surface of the tapered hole formed in the stem head in shape.

However it has still been impossible to prevent the development of cracks in the ceramic stem head and the reduction in bonding strength even by the above described means.

In addition, the ceramic stem head has a hardness remarkably higher than that of the metallic stem head and once the stem head is hammered onto the tapered cone of the pointed end portion of the metallic stem, the inner wall surface of the tapered hole of the stem head scrapes the metal cone and metallic debris is stuck to the inner wall surface of the tapered hole of the stem head to form black stains, whereby a large number of scratches and other irregularities are formed on the tapered cone at the pointed end of the metallic stem, and thus the engagement of the stem head with the tapered cone at the pointed end of the metallic stem is not fully realized even though the doctor has selected the stem and tapered cone, from among the many available, most suitable for the body structure of the patient. That it so say, the doctor has less chance to adequately select the most appropriate stem and tapered cone.

In addition, as proposed in U.S. patent application Ser. No. 07/370,450 in which the present inventor is one of co-inventors, it is desired in order to solve the above described problems that the angle of the tapered cone of the stem is set slightly smaller than that of the tapered hole formed in the ceramic stem head and the tapered cone at the pointed end of the stem is engaged with the depth or the wall surface of the tapered hole formed in the stem to prevent the stem head from being cracked and thereby increase the bonding strength. However, the problem remains that the metallic debris are ground onto the wall surface of the tapered hole of the ceramic stem head and the scratches abrasions and other irregularities can not be prevented from being generated on the tapered cone at the pointed end portion of the stem.

SUMMARY OF THE INVENTION

In order to solve the above described problems, according to the present invention, a truncated conical sleeve formed of pure titanium, titanium alloys and the like is disposed between the ceramic stem head and the tapered cone of the metallic stem and a thickness of the sleeve is reduced to deform the sleeve and absorb an error between both tapers, whereby intending to prevent the cracking of the stem head and increase the bonding strength.

The disposition of such the sleeve leads to the following effects:

① The taper angle of the tapered cone at the pointed end of the stem is set at about ⅛ to 1/20 times that of the tapered hole of the stem head to change the thickness of the truncated conical sleeve by about 200 μm, whereby the length of the stem neck of the artificial hip joint can be optionally changed, the preparation of many types of ceramic stem head being not required, that is merely one kind of ceramic stem head being sufficient, the productivity being improved, and both the quality and the strength being stabilized.

② The pointed end of the stem can be easily engaged with the depth of the tapered hole of the stem head by selectively changing the thickness of the truncated conical sleeve.

③ Formation of metallic debris can be prevented from adhering to the wall surface of the tapered hole of the ceramic stem head, and the generation of surface damage on the tapered cone at the pointed end portion of the metallic stem can be reduced.

The preferred embodiments of the present invention will be below described with reference to the drawings.

BRIEF DESCRIPTION OF THE DRAWINGS

Referring now to FIG. 1(A), B designates the stem head formed of alumina, zirconia ceramics and the like revolvably housed in the pelvis socket (not shown) and provided with a tapered hole b tapered toward the depth. S designates the stem fixedly inserted into a femur. The stem S is formed of metals, such as titanium alloys, cobalt-chrome alloys and stainless steels, and provided with a tapered portion T formed at a pointed end thereof. Said tapered portion T is inserted into the truncated conical sleeve L, which has been previously inserted into the tapered hole b of the stem head B, so as to be engaged with the inner wall of the truncated conical sleeve L. FIG. 1(B) is a perspective view three-dimensionally showing the truncated conical sleeve L.

In FIG. 2, the wall thickness of the truncated conical sleeve L is changed in two manners, that is changed thicker upward and thinner downward. The tapered portion T of the stem S is engaged with the tapered hole b at a position in the depth of the tapered hole b, whereby enhancing the fracture strength of the ceramic stem head B.

Figure 1:
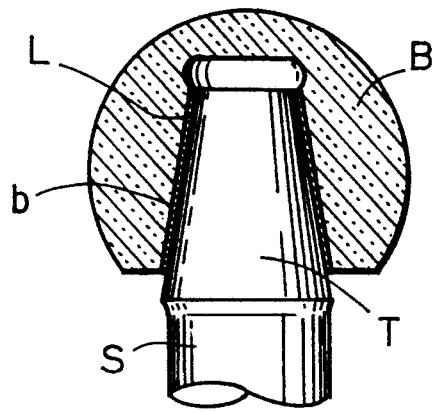
FIG. 1(A) is a sectional view showing principal parts in an artificial hip joint according to a preferred embodiment of the present invention.
FIG. 1(B) is a perspective view showing merely a truncated conical sleeve composing an artificial hip joint according to the preferred embodiment of the present invention.
Figure 1:
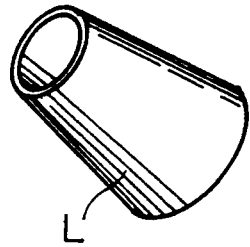
Figure 2:
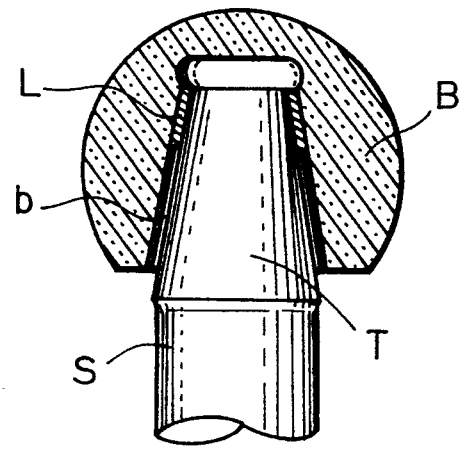
FIG. 2, and FIGS. 3(A), (B), (C) are all sectional views showing principal parts in an artificial hip joint according to other preferred embodiments.
Figure 3:
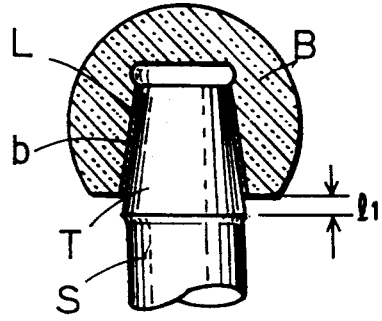
Figure 3:
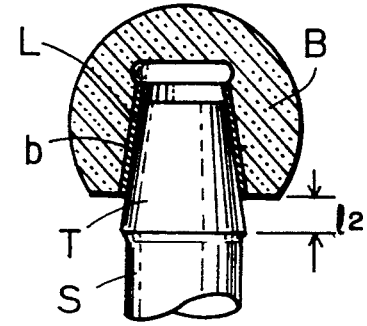
Figure 3:
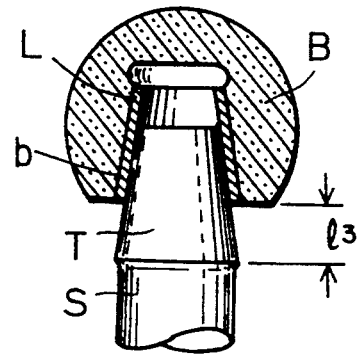

In addition, in FIG. 3(A), (B), (C) the whole wall thickness of the truncated conical sleeve L is varied, that is it is increased in the order of (A), (B), and (C), to regulate a length of the stem S to be inserted at $l_1$, $l_2$ and $l_3$, whereby being capable of mounting the artificial hip joint on the respective patients under the optimum condition.

It is necessary that there is no possibility that the above described truncated conical sleeve L damages the surface of the tapered portion T at the pointed end portion of the stem S, into which the truncated conical sleeve L is inserted. Accordingly, the stem S is in general formed of cobalt-chrome alloys having a hardness HRc (Rockwell hardness) of about 45 or titanium alloys having a hardness HRc of about 35, so that the truncated conical sleeve is formed of pure titanium having a hardness HRc of about 20, which is preferably less than the hardness HRc of the materials, of which the stem S is formed, gold, platinum or synthetic resins, such as polyethylene, having a hardness HRc, which is remarkably less than the hardness HRc of the materials, of which the stem S is formed; titanium alloys, cobalt-chrome alloys and stainless alloys having the same extent of hardness as that of said materials, and the like.

Figure 4:
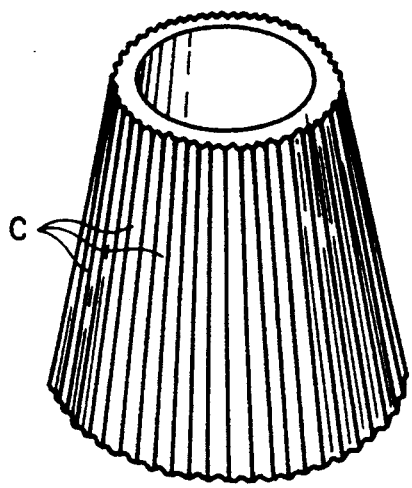
FIGS. 4(A), (B), (C) are all perspective views showing another embodiments of truncated conical sleeves.
Figure 4:
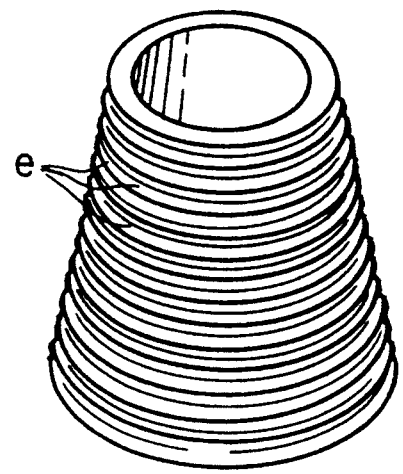
Figure 4:
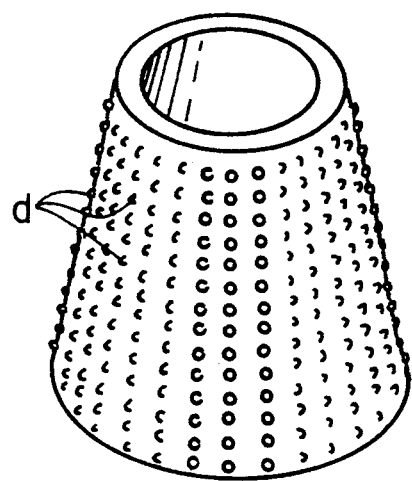

In addition, in order to enhance the engaging force of the truncated conical sleeve L with the hole wall surface of the tapered hole b of the ceramic stem head B, it has been experimentally confirmed that it is desirable to provide the surface of the sleeve L with a longitudinal convex member C, as shown in FIG. 4(A), to form an intermittent projecting wart member d, as shown in FIG. 4(B), or, to provide a continuous or discontinuous circumferential groove e, these measures being preferably able to be freely selected, and to select the height of said convex member C, said producting wart member d and the mountain of said circumferential groove e at 50 to 500 μm.

In addition, it is rational to select the thickness of the truncated conical sleeve L at 50 μm to 5.0 mm. If the thickness of the truncated conical sleeve L is 50 μm or less, the above described effects can not be sufficiently exhibited while if it is 5.0 mm or more, the tapered hole having a large diameter must be opened in the stem head and thus the wall thickness of the ceramic stem head B is reduced by the use of the sleeve, whereby remarkably reducing the strength which is very dangerous.

Figure 5:
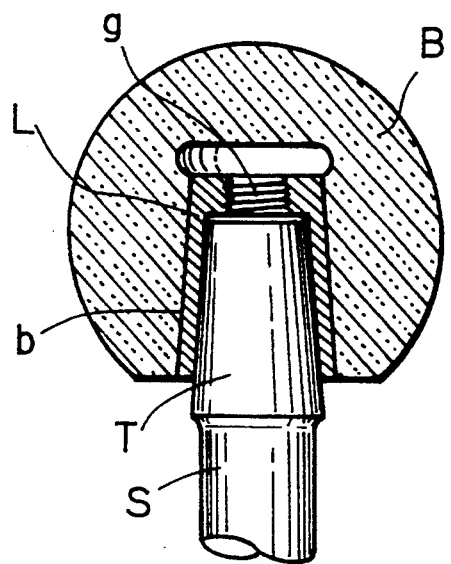
FIG. 5 is a sectional view showing principal parts in an artificial hip joint according to a modified preferred embodiment of the present invention.

FIG. 5 shows a modified preferred embodiment of the present invention. In this preferred embodiment, after the stem head B including the truncated conical sleeve L has been engaged with the tapered cone T of the stem S, the truncated conical sleeve L is removed. That is to say, as shown in FIG. 5, the top portion of the truncated conical sleeve L is closed by means of a top cover f and said top cover f has a female screw hole g therethrough at an almost center thereof.

Figure 6:
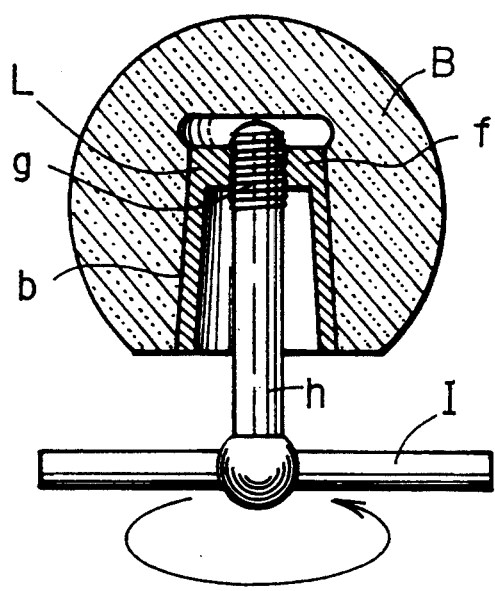
FIG. 6(A), (B) is a sectional view showing the procedure to remove the truncated conical sleeve of the artificial hip joint shown in FIG. 5.
Figure 6:
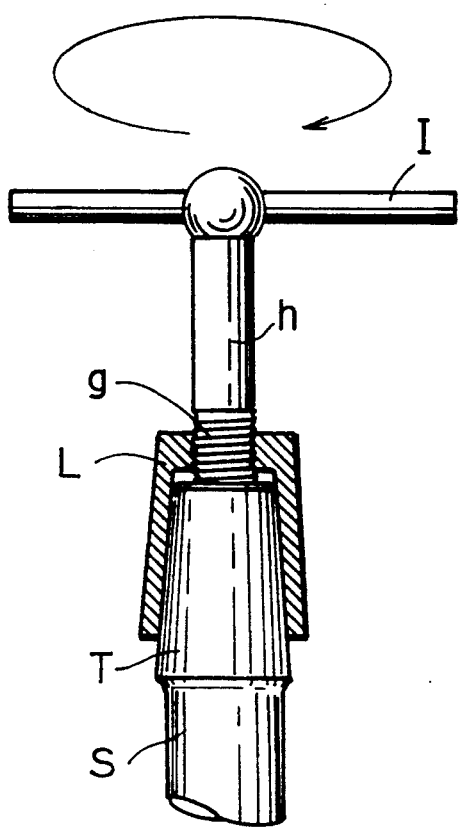

A method of removing the truncated conical sleeve L by the use of such the female screw hole g is shown in FIG. 6(A), (Y). In the case where the stem head B is compressedly engaged with the tapered cone T, said truncated conical sleeve L is in the condition that it is compressedly engaged with the stem head B or the condition that it is compressedly engaged with the tapered cone T of the stem S. FIG. 6(A) shows the former example in which a screw lever h is screwed in said concave screw hole g by means of a rotary remover I provided with said screw lever h to be screwed in said female screw hole g to draw down the truncated conical sleeve L along the tapered hole b, whereby removing the truncated conical sleeve L. FIG. 6(B) shows a method in which said screw lever h is screwed in the female screw hole g of the top cover f of the truncated conical sleeve L pressedly engaged with the tapered cone of the stem S from above to draw up the truncated conical sleeve L, whereby removing the trancated conical sleeve L. It will be understood that such the easy removability of the truncated conical sleeve L is advantageous in not only the operation but also the case where the stem head B and the truncated conical sleeve L are exchanged by the reoperation after the lapse of time since the first operation.

As above described, according to the present invention, the disposition of the truncated conical sleeve between the ceramic stem head and the metallic stem leads to the following effects:

① The variation of the angle between both tapers can be absorbed by the deformation of the flexible metal, whereby remarkably increasing the strength of the stem head.

② The dislocation of both tapered surfaces to each other can be absorbed to some extent, whereby the manufactural control is remarkably easy.

③ The strength of the stem head is increased to reduce the diameter of the stem, whereby sufficiently increasing the wall thickness of high-density polyethylene and the like forming the sliding surface of the pelvis socket and thus increasing an useful life time of the artificial hip joint.

④ The adherence of metals to the inner wall surface of the tapered hole opened in the stem head or the generation of damage in the tapered cone of the metallic stem is reduced, so that the safety in operation can be increased.

Accordingly, the present invention can provide the artificial hip joint having a high productivity, a high strength, a long useful life time and a high reliability, and thus can greatly contribute to orthopedical restorements.

What is claimed is:

1. An artificial hip joint, comprising:
   a ceramic head having a tapered bore therein, said tapered bore having an entrance;
   a metal stem having a tapered portion formed at one end thereof, the tapered portion configured to be inserted in the tapered bore in the head; and
   a truncated conical sleeve having a wall thickness in the range of about 50 μm to 5.0 mm, wherein the sleeve is compressed between the tapered bore in the head and the tapered portion of the stem forming a tapered fit;
   wherein the thickness of the wall is varied along a longitudinal axis of the sleeve such that the wall has an upper segment having an increased wall thickness at an upper end of said sleeve, and a lower segment having a reduced wall thickness at a lower end of said sleeve such that when the tapered portion is inserted into the sleeve there is a tight fit between the tapered portion and the upper segment and a loose connection between the tapered portion and the lower segment.

2. An artificial hip joint according to claim 1, wherein the ceramic head is formed of one of alumina ceramics and zirconia ceramics, the metallic stem is formed of one of titanium alloys, cobalt-chrome alloys and stainless steels, and said truncated conical sleeve is formed of one of pure titanium, titanium alloys, cobalt-chrome alloys, stainless steel alloys, gold, platinum and polyethylene.

3. An artificial hip joint according to claim 1, wherein a proximal end of said truncated conical sleeve is open.

4. An artificial hip joint according to claim 2, wherein said truncated conical sleeve is formed of metal having a hardness less than that of the metal of the stem.

5. An artificial hip joint according to claim 4, wherein the stem is formed of one of Co—Cr alloy and titanium alloys, and said truncated conical sleeve is formed of one of pure titanium, gold, and platinum.

6. An artificial hip joint comprising:
   a ceramic head having a tapered bore therein, said tapered bore having an entrance portion and an upper end portion;
   a metal stem having a tapered portion formed at one end thereof, the tapered portion configured to be inserted in the tapered bore in the head; and
   a truncated conical sleeve, wherein the sleeve is compressed between the tapered bore in the head and the tapered portion of the stem forming a tapered fit;
   wherein the sleeve is brought into close engagement with the tapered portion in an area adjacent to the upper end portion of the tapered bore and loose engagement with the tapered portion in an area adjacent to the entrance thereof, wherein the sleeve has a greater wall thickness in the area adjacent to the upper end portion of the tapered bore than a wall thickness in the area adjacent to the entrance of the tapered bore.

* * * * *